(12) United States Patent
Patterson et al.

(10) Patent No.: US 8,017,331 B2
(45) Date of Patent: Sep. 13, 2011

(54) IRE-1α SUBSTRATES

(75) Inventors: John Bruce Patterson, Ventura, CA (US); Kori Shallyn Volkmann, Canyon County, CA (US); Duane Brumm, Newbury Park, CA (US); Caryn Stiles, Pasadena, CA (US)

(73) Assignee: MannKind Corporation, Valencia, CA (US)

( * ) Notice: Subject to any disclaimer, the term of this patent is extended or adjusted under 35 U.S.C. 154(b) by 994 days.

(21) Appl. No.: 11/266,603

(22) Filed: Nov. 4, 2005

(65) Prior Publication Data

US 2007/0105123 A1    May 10, 2007

(51) Int. Cl.
C12Q 1/68    (2006.01)
C07H 21/04    (2006.01)

(52) U.S. Cl. ........................ 435/6.1; 536/24.3
(58) Field of Classification Search .......................... None
See application file for complete search history.

(56) References Cited

U.S. PATENT DOCUMENTS

| | | | | | |
|---|---|---|---|---|---|
| 5,582,993 | A | * | 12/1996 | Stackebrandt et al. | 435/6 |
| 5,610,012 | A | * | 3/1997 | Luchansky et al. | 435/6 |
| 5,871,983 | A | * | 2/1999 | Baltz et al. | 435/486 |
| 5,925,517 | A | * | 7/1999 | Tyagi et al. | 435/6 |
| 6,566,058 | B1 | * | 5/2003 | Cardy | 435/6 |
| 2002/0187484 | A1 | * | 12/2002 | Thorson et al. | 435/6 |
| 2003/0064366 | A1 | * | 4/2003 | Hardin et al. | 435/6 |

FOREIGN PATENT DOCUMENTS

JP    11056398 A  *  3/1999

OTHER PUBLICATIONS

Calfon et al. ("IRE1 couples endoplasmic reticulum load to secretory capacity by processing the XBP-1 mRNA" Nature. Jan. 3, 2002;415(6867):92-6).*
Lee et al. ("IRE1-mediated unconventional mRNA splicing and S2P-mediated ATF6 cleavage merge to regulate XBP1 in signaling the unfolded protein response" Genes Dev. Feb. 15, 2002;16(4):452-66).*
Nilsson et al. (Nucleic Acids Res. Jul. 15, 2002;30(14)).*
Gonzalez et al. ("Mechanism of non-spliceosomal mRNA splicing in the unfolded protein response pathway" The EMBO Journal 18, 3119-32, 1999).*
Rizzo et al. ("Chimeric RNA-DNA molecular beacon assay for ribonuclease H activity" Molecular and Cellular Probes, Aug. 2002, 16(4):277-83).*
Bertolotti & Ron, "Alterations in an IRE1-RNA complex in the mammalian unfolded protein response," J. Cell Sci 114, 3207-12, 2001.
Calfon et al., "IRE1 couples endoplasmic reticulum load to secretory capacity by processing the XBP-1 mRNA," Nature 415, 92-96, Jan. 3, 2002.
Dong et al., "Basis for regulated RNA cleavage by functional analysis of RNase L and Ire1p," RNA 7, 361-73, 2001.
Gonzalez et al., "Mechanism of non-spliceosomal mRNA splicing in the unfolded protein response pathway," The EMBO Journal 18, 3119-32, 1999.
Iwawaki et al., "A transgenic mouse model for monitoring endoplasmic reticulum stress," Nature Med. 10, 98-102, Jan. 2004.
Kaufman, "Orchestrating the unfolded protein response in health and disease," J. Clin. Investigation 110, 1389-98, 2002.
Lee et al., "IRE1-mediated unconventional mRNA splicing and S2P-mediated ATF6 cleavage merge to regulate XBP1 in signaling the unfolded protein response," Genes & Development 16, 452-66, 2002.
Lee et al., "XBP-1 Regulates a Subset of Endoplasmic Reticulum Resident Chaperone Genes in the Unfolded Protein Response," Mol. Cell. Biol 23, 7448-59, Nov. 2003.
Liu et al., "The Protein Kinase/Endoribonuclease IRE1α That Signals the Unfolded Protein Response Has a Luminal N-terminal Ligand-independent Dimerization Domain," J. Biol. Chem. 277, 18346-56, 2002, May 24, 2002.
Liu et al., "Ligand-independent Dimerization Activates the Stress Response Kinases IRE1 and PERK in the Lumen of the Endoplasmic Reticulum," J. Biol. Chem. 275, 24881-85, Aug. 11, 2000.
Niwa et al., "Genome-scale approaches for discovering novel nonconventional splicing substrates of the Ire1 nuclease," Genome Biology 6, R3, 2004.
Tirasophon et al., "The endoribonuclease activity of mammalian IRE1 autoregulates its mRNA and is required for the unfolded protein response," Genes & Devel. 14, 2725-36, 2000.
Li et al., "Targeting degradation of RNA by RNase H using DNA hairpins", Biochemistry, Sep. 23, 2003, 42(37):10945-54.
Rizzo et al., "Chimeric RNA-DNA molecular beacon assay for ribonuclease H activity", Molecular and Cellular Probes, Aug. 2002, 16(4):277-83.
Lee et al., "Structure of the Dual Enzyme Ire1 Reveals the Basis for Catalysis and Regulation in Nonconventional RNA Splicing," Cell 132, 89-100, Jan. 11, 2008.
Tirasophon et al., "A stress response pathway from the endoplasmic reticulum to the nucleus requires a novel bifunctional protein kinase/endoribonuclease (Ire1p) in mammalian cells," Genes Devel. 12, 1812-24, 1998.
Tyagi, "Designing Molecular Beacons," downloaded Sep. 3, 2009 from www.molecularbeacons.org, Public Health Research Institute, University of Medicine and Dentistry, New Jersey, 4 pages; undated, but no earlier than 2004.
Vet & Marras, "Design and optimization of molecular beacon real-time polymerase chain reaction assays," In Herdewijn, P. (ed.), Oligonucleotide synthesis: Methods and Applications, Humana Press, Totowa, NJ, vol. 288, pp. 273-290, 2004.
Saunders & Barber, "The dsRNA binding protein family: critical roles, diverse cellular functions," FASEB Journal 17, 961-83, Jun. 2003. Aguirre-Hernández et al., "Computational RNA secondary structure design: empirical complexity and improved methods," BMC Bioinformatics 8, 34-50, 2007.
Alexopoulou et al., "Recognition of double-stranded RNA and activation of NF-κB by Toll-like receptor 3," Nature 413, 732-38 2001.
Becker et al., "Major Identity Determinants for Enzymatic Formation of Ribothymidine and Pseudouridine in the TΨ-loop of Yeast tRNAs," J. Mol. Biol. 274, 505-18, 1997.
Biou et al., "The 2.9 Å Crystal Structure of T. thermophilus Seryl-tRNA Synthetase Complexed with tRNA$^{Ser}$," Science 263, 1404-10, 1994.
Calfon et al., "IRE1 couples endoplasmic reticulum load to secretory capacity by processing the XBP-1 mRNA," Nature 415, 92-96, 2002.
Cavarelli et al., "The active site of yeast aspartyl-tRNA synthetase: structural and functional aspects of the aminoacylation reaction," The EMBO Journal 13, 327-37, 1994.

(Continued)

Primary Examiner — Christopher M. Babic
(74) Attorney, Agent, or Firm — Banner & Witcoff, Ltd.

(57) ABSTRACT

IRE-1α substrates useful for identifying agonists and antagonists of IRE-1α RNase activity.

52 Claims, 7 Drawing Sheets

OTHER PUBLICATIONS

Conn et al., "Crystal Structure of a Conserved Ribosomal Protein-RNA Complex," Science 284, 1171-74, 1999.
Ferré-D'Amaré, "RNA-modifying enzymes," Curr. Opin. Structural Biol. 13, 49-55, 2003.
Gu et al., "Molecular Recognition of tRNA by tRNA Pseudouridine 5S Synthase," Biochem. 37, 339-43, 1998.
Hamma & Ferré-D'Amaré, "Pseudouridine Synthases," Chem. & Biol. 13, 1125-35, 2006.
Larkin et al., "Identification of essential domains for *Escherichia coli* tRNA$^{leu}$ aminoacylation and amino acid editing using minimalist RNA molecules," Nucl. Acids Res. 30, 2103-13, 2002.
Martinis & Schimmel, "Enzymatic aminoacylation of sequence-specific RNA minihelices and hybrid duplexes with methionine," Proc. Natl. Acad. Sci. (USA) 89, 65-69, 1992.
Mu et al., "Structure of the Ire1 autophosphorylation complex and implications for the unfolded protein response," The EMBO J. "EMBO open" (2011), 1-12.
Nissen et al., "Crystal Structure of the Ternary Complex of Phe-tRNA$^{Phe}$, EF-Tu, and a GTP Analog," Science 270, 1464-72, 1995.
Pan et al., "Structure of tRNA pseudouridine synthase TruB and its RNA complex: RNA recognition through a combination of rigid docking and induced fit," Proc. Natl. Acad. Sci. (USA) 100, 12648-53, 2003.
Pan et al., "How the CCA-Adding Enzyme Selects Adenine over Cytosine at Position 76 of tRNA," Science 330, 937-40, 2010.
Ritchie et al., "RNA stem-loops: To be or not to be cleaved by RNAse III," RNA 13, 457-62, 2007.
Saunders & Barber, "The dsRNA binding protein family: critical roles, diverse cellular functions," FASEB J. 17, 961-83, 2003.
Schmitt et al., "Crystal structure of methionyl-tRNA$^{Met}_f$ transformylase complexed with the initiator formyl-methionyl-tRNA$^{Met}_f$," The EMBO Journal 17, 6819-26, 1998.
Shi et al., "RNA Tetraloops as Minimalist Substrates for Aminoacylation," Biochem. 31, 4931-36, 1992.
Silvian et al, "Insights into Editing from an Ile-tRNA Synthetase Structure with tRNA$^{Ile}$ and Mupirocin," Science 285, 1074-77, 1999.
Tomita et al., "Complete crystallographic analysis of the dynamics of CCA sequence addition," (2006) Nature 443: 956-960.
Wu et al., "Structural basis for recognition of the AGNN tetraloop RNA fold by the double-stranded RNA-binding domain of Rnt1p RNase III," Proc. Natl. Acad. Sci. (USA) 101, 8307-12, 2004.
Xiong & Steitz, "Mechanism of transfer RNA maturation by CCA-adding enzyme without using an oligonucleotide template," (2004) Nature 430: 640-645.
Xue et al., "RNA Recognition and Cleavage by a Splicing Endonuclease," Science 312, 906-10, 2006.

* cited by examiner

SEQUENCE LISTING

<160> NUMBER OF SEQ ID NOS: 15

<210> SEQ ID NO 1
<211> LENGTH: 33
<212> TYPE: DNA
<213> ORGANISM: Artificial Sequence
<220> FEATURE:
<223> OTHER INFORMATION: IRE-1alpha substrate

<400> SEQUENCE: 1
gggucugcug aguccgcagc acucagaagg ccc         33

<210> SEQ ID NO 2
<211> LENGTH: 33
<212> TYPE: DNA
<213> ORGANISM: Artificial Sequence
<220> FEATURE:
<223> OTHER INFORMATION: IRE-1alpha substrate

<400> SEQUENCE: 2
gggucugcug agucccagc acucagaagg ccc          33

<210> SEQ ID NO 3
<211> LENGTH: 15
<212> TYPE: DNA
<213> ORGANISM: Artificial Sequence
<220> FEATURE:
<223> OTHER INFORMATION: IRE-1alpha substrate

<400> SEQUENCE: 3
caguccgcag cacug                              15

<210> SEQ ID NO 4
<211> LENGTH: 15
<212> TYPE: DNA
<213> ORGANISM: Artificial Sequence
<220> FEATURE:
<223> OTHER INFORMATION: IRE-1alpha substrate

<400> SEQUENCE: 4 cagucccag cacug                               15

<210> SEQ ID NO 5
<211> LENGTH: 11
<212> TYPE: DNA
<213> ORGANISM: Artificial Sequence
<220> FEATURE:
<223> OTHER INFORMATION: IRE-1alpha substrate

<400> SEQUENCE: 5
cuccccagca g                                  11

```
<210> SEQ ID NO 6
<211> LENGTH: 11
<212> TYPE: DNA
<213> ORGANISM: Artificial Sequence
<220> FEATURE:
<223> OTHER INFORMATION: IRE-1alpha substrate

<400> SEQUENCE: 6
cuccgcagca g                                                            11

<210> SEQ ID NO 7
<211> LENGTH: 749
<212> TYPE: PRT
<213> ORGANISM: Artificial Sequence
<220> FEATURE:
<223> OTHER INFORMATION: IRE-1alpha-GST fusion protein

<400> SEQUENCE: 7
```

Ser Pro Ile Leu Gly Tyr Trp Lys Ile Lys Gly Leu Val Gln Pro Thr
1               5                   10                  15

Arg Leu Leu Leu Glu Tyr Leu Glu Glu Lys Tyr Glu Glu His Leu Tyr
            20                  25                  30

Glu Arg Asp Glu Gly Asp Lys Trp Arg Asn Lys Lys Phe Glu Leu Gly
        35                  40                  45

Leu Glu Phe Pro Asn Leu Pro Tyr Tyr Ile Asp Gly Asp Val Lys Leu
    50                  55                  60

Thr Gln Ser Met Ala Ile Ile Arg Tyr Ile Ala Asp Lys His Asn Met
65                  70                  75                  80

Leu Gly Gly Cys Pro Lys Glu Arg Ala Glu Ile Ser Met Leu Glu Gly
                85                  90                  95

Ala Val Leu Asp Ile Arg Tyr Gly Val Ser Arg Ile Ala Tyr Ser Lys
            100                 105                 110

Asp Phe Glu Thr Leu Lys Val Asp Phe Leu Ser Lys Leu Pro Glu Met
        115                 120                 125

Leu Lys Met Phe Glu Asp Arg Leu Cys His Lys Thr Tyr Leu Asn Gly
    130                 135                 140

Asp His Val Thr His Pro Asp Phe Met Leu Tyr Asp Ala Leu Asp Val
145                 150                 155                 160

Val Leu Tyr Met Asp Pro Met Cys Leu Asp Ala Phe Pro Lys Leu Val
                165                 170                 175

Cys Phe Lys Lys Arg Ile Glu Ala Ile Pro Gln Ile Asp Lys Tyr Leu
            180                 185                 190

Lys Ser Ser Lys Tyr Ile Ala Trp Pro Leu Gln Gly Trp Gln Ala Thr
        195                 200                 205

Phe Gly Gly Gly Asp His Pro Pro Lys Ser Asp Leu Glu Val Leu Phe
    210                 215                 220

Gln Gly Pro Leu Gly Ser Pro Glu Phe Ile Thr Tyr Pro Leu Ser Met
225                 230                 235                 240

His Gln Gln Gln Leu Gln His Gln Phe Gln Lys Glu Leu Glu
                245                 250                 255

Lys Ile Gln Leu Leu Gln Gln Gln Gln Gln Leu Pro Phe His Pro
            260                 265                 270

Pro Gly Asp Thr Ala Gln Asp Gly Glu Leu Leu Asp Thr Ser Gly Pro
        275                 280                 285

Tyr Ser Glu Ser Ser Gly Thr Ser Ser Pro Thr Ser Pro Arg Ala
        290                 295                 300

Ser Asn His Ser Leu Cys Ser Gly Ser Ser Ala Ser Lys Ala Gly Ser
305                 310                 315                 320

```
Ser Pro Ser Leu Glu Gln Asp Asp Gly Asp Glu Thr Ser Val Val
            325                 330                 335

Ile Val Gly Lys Ile Ser Phe Cys Pro Lys Asp Val Leu Gly His Gly
            340                 345                 350

Ala Glu Gly Thr Ile Val Tyr Arg Gly Met Phe Asp Asn Arg Asp Val
            355                 360                 365

Ala Val Lys Arg Ile Leu Pro Glu Cys Phe Ser Phe Ala Asp Arg Glu
            370                 375                 380

Val Gln Leu Leu Arg Glu Ser Asp Glu His Pro Asn Val Ile Arg Tyr
385                 390                 395                 400

Phe Cys Thr Glu Lys Asp Arg Gln Phe Gln Tyr Ile Ala Ile Glu Leu
            405                 410                 415

Cys Ala Ala Thr Leu Gln Glu Tyr Val Glu Gln Lys Asp Phe Ala His
            420                 425                 430

Leu Gly Leu Glu Pro Ile Thr Leu Leu Gln Gln Thr Thr Ser Gly Leu
            435                 440                 445

Ala His Leu His Ser Leu Asn Ile Val His Arg Asp Leu Lys Pro His
            450                 455                 460

Asn Ile Leu Ile Ser Met Pro Asn Ala His Gly Lys Ile Lys Ala Met
465                 470                 475                 480

Ile Ser Asp Phe Gly Leu Cys Lys Lys Leu Ala Val Gly Arg His Ser
            485                 490                 495

Phe Ser Arg Arg Ser Gly Val Pro Gly Thr Glu Gly Trp Ile Ala Pro
            500                 505                 510

Glu Met Leu Ser Glu Asp Cys Lys Glu Asn Pro Thr Tyr Thr Val Asp
            515                 520                 525

Ile Phe Ser Ala Gly Cys Val Phe Tyr Tyr Val Ile Ser Glu Gly Ser
            530                 535                 540

His Pro Phe Gly Lys Ser Leu Gln Arg Gln Ala Asn Ile Leu Leu Gly
545                 550                 555                 560

Ala Cys Ser Leu Asp Cys Leu His Pro Glu Lys His Glu Asp Val Ile
            565                 570                 575

Ala Arg Glu Leu Ile Glu Lys Met Ile Ala Met Asp Pro Gln Lys Arg
            580                 585                 590

Pro Ser Ala Lys His Val Leu Lys His Pro Phe Phe Trp Ser Leu Glu
            595                 600                 605

Lys Gln Leu Gln Phe Phe Gln Asp Val Ser Asp Arg Ile Glu Lys Glu
            610                 615                 620

Ser Leu Asp Gly Pro Ile Val Lys Gln Leu Glu Arg Gly Gly Arg Ala
625                 630                 635                 640

Val Val Lys Met Asp Trp Arg Glu Asn Ile Thr Val Pro Leu Gln Thr
            645                 650                 655

Asp Leu Arg Lys Phe Arg Thr Tyr Lys Gly Gly Ser Val Arg Asp Leu
            660                 665                 670

Leu Arg Ala Met Arg Asn Lys Lys His His Tyr Arg Glu Leu Pro Ala
            675                 680                 685

Glu Val Arg Glu Thr Leu Gly Ser Leu Pro Asp Asp Phe Val Cys Tyr
            690                 695                 700

Phe Thr Ser Arg Phe Pro His Leu Leu Ala His Thr Tyr Arg Ala Met
705                 710                 715                 720

Glu Leu Cys Ser His Glu Arg Leu Phe Gln Pro Tyr Tyr Phe His Glu
            725                 730                 735

Pro Pro Glu Pro Gln Pro Pro Val Thr Pro Asp Ala Leu
```

<210> SEQ ID NO 8
<211> LENGTH: 2253
<212> TYPE: DNA
<213> ORGANISM: Artificial Sequence
<220> FEATURE:
<223> OTHER INFORMATION: nucleotide sequence encoding SEQ ID NO:7

<400> SEQUENCE: 8

| | | | | | |
|---|---|---|---|---|---|
| atgtcccta | tactaggtta | ttggaaaatt | aagggccttg | tgcaacccac | tcgacttctt | 60 |
| ttggaatatc | ttgaagaaaa | atatgaagag | catttgtatg | agcgcgatga | aggtgataaa | 120 |
| tggcgaaaca | aaaagtttga | attgggtttg | gagtttccca | atcttcctta | ttatattgat | 180 |
| ggtgatgtta | aattaacaca | gtctatggcc | atcatacgtt | atatagctga | caagcacaac | 240 |
| atgttgggtg | ttgtccaaa | agagcgtgca | gagatttcaa | tgcttgaagg | agcggttttg | 300 |
| gatattagat | acggtgtttc | gagaattgca | tatagtaaag | actttgaaac | tctcaaagtt | 360 |
| gattttctta | gcaagctacc | tgaaatgctg | aaaatgttcg | aagatcgttt | atgtcataaa | 420 |
| acatatttaa | atggtgatca | tgtaacccat | cctgacttca | tgttgtatga | cgctcttgat | 480 |
| gttgttttat | acatggaccc | aatgtgcctg | gatgcgttcc | caaaattagt | ttgtttaaa | 540 |
| aaacgtattg | aagctatccc | acaaattgat | aagtacttga | atccagcaa | gtatatagca | 600 |
| tggcctttgc | agggctggca | agccacgttt | ggtggtggcg | accatcctcc | aaaatcggat | 660 |
| ctggaagttc | tgttccaggg | gcccctggga | tccccggaat | tcatcaccta | tcccctgagc | 720 |
| atgcatcagc | agcagcagct | ccagcaccag | cagttccaga | aggaactgga | gaagatccag | 780 |
| ctcctgcagc | agcagcagca | gcagctgccc | ttccacccac | ctggagacac | ggctcaggac | 840 |
| ggcgagctcc | tggacacgtc | tggcccgtac | tcagagagct | cgggcaccag | cagccccagc | 900 |
| acgtccccca | gggcctccaa | ccactcgctc | tgctccggca | gctctgcctc | caaggctggc | 960 |
| agcagcccct | ccctggaaca | gacgatgga | gatgaggaaa | ccagcgtggt | gatagttggg | 1020 |
| aaaatttcct | tctgtcccaa | ggatgtcctg | ggccatggag | ctgagggcac | aattgtgtac | 1080 |
| cggggcatgt | ttgacaaccg | cgacgtggcc | gtgaagagga | tcctcccga | gtgttttagc | 1140 |
| ttcgcagacc | gtgaggtcca | gctgttgcga | gaatcggatg | agcacccgaa | cgtgatccgc | 1200 |
| tacttctgca | cggagaagga | ccggcaattc | cagtacattg | ccatcgagct | gtgtgcagcc | 1260 |
| accctgcaag | agtatgtgga | gcagaaggac | tttgcgcatc | tcggcctgga | gcccatcacc | 1320 |
| ttgctgcagc | agaccaccte | gggcctggcc | cacctccact | ccctcaacat | cgttcacaga | 1380 |
| gacctaaagc | cacacaacat | cctcatatcc | atgcccaatg | cacacggcaa | gatcaaggcc | 1440 |
| atgatctccg | actttggcct | ctgcaagaag | ctggcagtgg | gcagacacag | tttcagccgc | 1500 |
| cgatctgggg | tgcctggcac | agaaggctgg | atcgctccag | agatgctgag | cgaagactgt | 1560 |
| aaggagaacc | ctacctacac | ggtggacatc | ttttctgcag | gctgcgtctt | ttactacgta | 1620 |
| atctctgagg | gcagccaccc | ttttggcaag | tccctgcagc | ggcaggccaa | catcctcctg | 1680 |
| ggtgcctgca | gccttgactg | cttgcaccca | gagaagcacg | aagacgtcat | tgcacgtgaa | 1740 |
| ttgatagaga | agatgattgc | gatggatcct | cagaaacgcc | cctcagcgaa | gcacgtgctc | 1800 |
| aaacacccgt | tcttctggag | cctagagaag | cagctccagt | tcttccagga | cgtgagcgac | 1860 |
| agaatagaaa | aggaatccct | ggatggcccg | atcgtgaagc | agttagagag | aggcgggaga | 1920 |
| gccgtggtga | gatggactg | gcgggagaac | atcactgtcc | cctccagac | agacctgcgt | 1980 |
| aaattcagga | cctataaagg | tggttctgtc | agagatctcc | tccgagccat | gagaaataag | 2040 |

```
aagcaccact accgggagct gcctgcagag gtgcgggaga cgctggggtc cctccccgac    2100
gacttcgtgt gctacttcac gtctcgcttc ccccacctcc tcgcacacac ctaccgggcc    2160
atggagctgt gcagccacga gagactcttc cagccctact acttccacga gccccagag    2220 ccccagcccc cagtgactcc agacgccctc tga                                 2253
```

<210> SEQ ID NO 9
<211> LENGTH: 225
<212> TYPE: PRT
<213> ORGANISM: Discosoma sp.

<400> SEQUENCE: 9

```
Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 10
<211> LENGTH: 18
<212> TYPE: PRT
<213> ORGANISM: Artificial Sequence
<220> FEATURE:
<223> OTHER INFORMATION: peptide linker

<400> SEQUENCE: 10

```
Gly Ser Thr Ser Gly Ser Gly Lys Pro Gly Ser Gly Glu Gly Ser Thr
 1               5                  10                  15

Lys Gly
```

<210> SEQ ID NO 11
<211> LENGTH: 238
<212> TYPE: PRT

<213> ORGANISM: Aequorea victoria

<400> SEQUENCE: 11

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 12
<211> LENGTH: 239
<212> TYPE: PRT
<213> ORGANISM: Aequorea victoria

<400> SEQUENCE: 12

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 13
<211> LENGTH: 239
<212> TYPE: PRT
<213> ORGANISM: Aequorea victoria

<400> SEQUENCE: 13

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 14
<211> LENGTH: 239
<212> TYPE: PRT
<213> ORGANISM: Aequorea victoria

```
<400> SEQUENCE: 14

Met Val Ser Lys Gly Glu Glu Leu Phe Thr Gly Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Phe Gly Tyr Gly Leu Lys Cys Phe Ala Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 15
<211> LENGTH: 524
<212> TYPE: PRT
<213> ORGANISM: Homo sapiens

<400> SEQUENCE: 15

Gly Pro Leu Gly Ser Pro Glu Phe Ile Thr Tyr Pro Leu Ser Met His
 1               5                  10                  15

Gln Gln Gln Gln Leu Gln His Gln Gln Phe Gln Lys Glu Leu Glu Lys
                20                  25                  30

Ile Gln Leu Leu Gln Gln Gln Gln Gln Leu Pro Phe His Pro Pro
            35                  40                  45

Gly Asp Thr Ala Gln Asp Gly Glu Leu Leu Asp Thr Ser Gly Pro Tyr
 50                  55                  60

Ser Glu Ser Ser Gly Thr Ser Ser Pro Ser Thr Ser Pro Arg Ala Ser
 65                  70                  75                  80

Asn His Ser Leu Cys Ser Gly Ser Ala Ser Lys Ala Gly Ser Ser
                85                  90                  95

Pro Ser Leu Glu Gln Asp Asp Gly Asp Glu Thr Ser Val Val Ile
            100                 105                 110

Val Gly Lys Ile Ser Phe Cys Pro Lys Asp Val Leu Gly His Gly Ala
        115                 120                 125
```

```
Glu Gly Thr Ile Val Tyr Arg Gly Met Phe Asp Asn Arg Asp Val Ala
        130                 135                 140
Val Lys Arg Ile Leu Pro Glu Cys Phe Ser Phe Ala Asp Arg Glu Val
145                 150                 155                 160
Gln Leu Leu Arg Glu Ser Asp Glu His Pro Asn Val Ile Arg Tyr Phe
                165                 170                 175
Cys Thr Glu Lys Asp Arg Gln Phe Gln Tyr Ile Ala Ile Glu Leu Cys
            180                 185                 190
Ala Ala Thr Leu Gln Glu Tyr Val Gln Lys Asp Phe Ala His Leu
        195                 200                 205
Gly Leu Glu Pro Ile Thr Leu Leu Gln Gln Thr Thr Ser Gly Leu Ala
    210                 215                 220
His Leu His Ser Leu Asn Ile Val His Arg Asp Leu Lys Pro His Asn
225                 230                 235                 240
Ile Leu Ile Ser Met Pro Asn Ala His Gly Lys Ile Lys Ala Met Ile
                245                 250                 255
Ser Asp Phe Gly Leu Cys Lys Lys Leu Ala Val Gly Arg His Ser Phe
            260                 265                 270
Ser Arg Arg Ser Gly Val Pro Gly Thr Glu Gly Trp Ile Ala Pro Glu
    275                 280                 285
Met Leu Ser Glu Asp Cys Lys Glu Asn Pro Thr Tyr Thr Val Asp Ile
290                 295                 300
Phe Ser Ala Gly Cys Val Phe Tyr Tyr Val Ile Ser Glu Gly Ser His
305                 310                 315                 320
Pro Phe Gly Lys Ser Leu Gln Arg Gln Ala Asn Ile Leu Leu Gly Ala
                325                 330                 335
Cys Ser Leu Asp Cys Leu His Pro Glu Lys His Glu Asp Val Ile Ala
            340                 345                 350
Arg Glu Leu Ile Glu Lys Met Ile Ala Met Asp Pro Gln Lys Arg Pro
        355                 360                 365
Ser Ala Lys His Val Leu Lys His Pro Phe Phe Trp Ser Leu Glu Lys
370                 375                 380
Gln Leu Gln Phe Phe Gln Asp Val Ser Asp Arg Ile Glu Lys Glu Ser
385                 390                 395                 400
Leu Asp Gly Pro Ile Val Lys Gln Leu Glu Arg Gly Gly Arg Ala Val
                405                 410                 415
Val Lys Met Asp Trp Arg Glu Asn Ile Thr Val Pro Leu Gln Thr Asp
            420                 425                 430
Leu Arg Lys Phe Arg Thr Tyr Lys Gly Gly Ser Val Arg Asp Leu Leu
        435                 440                 445
Arg Ala Met Arg Asn Lys Lys His His Tyr Arg Glu Leu Pro Ala Glu
    450                 455                 460
Val Arg Glu Thr Leu Gly Ser Leu Pro Asp Asp Phe Val Cys Tyr Phe
465                 470                 475                 480
Thr Ser Arg Phe Pro His Leu Leu Ala His Thr Tyr Arg Ala Met Glu
                485                 490                 495
Leu Cys Ser His Glu Arg Leu Phe Gln Pro Tyr Tyr Phe His Glu Pro
            500                 505                 510
Pro Glu Pro Gln Pro Pro Val Thr Pro Asp Ala Leu
        515                 520
```

IRE-1α SUBSTRATES

FIELD OF THE INVENTION

The invention relates to substrates for IRE-1α.

BACKGROUND OF THE INVENTION

The unfolded protein response (UPR) is an intracellular signaling pathway which responds to the accumulation of misfolded proteins in the endoplasmic reticulum (ER) lumen. The UPR is increasingly recognized as a significant factor in many human diseases. Up-regulation of the UPR is thought to be important for tumor survival and B-cell autoimmunity, whereas UPR suppression is implicated in diseases such as Alzheimer's disease and type II diabetes.

IRE-1α is a transmembrane signaling molecule with an N-terminal luminal domain inside the ER and a C-terminal kinase and RNase domain in the cytosol. The N-terminal luminal domain complexes with GRP78. IRE-1α is an ER stress sensor. When activated, IRE-1α induces transcription of endoplasmic reticulum stress response genes, such as GRP78 and GRP94, by activating the transcription factor XBP-1 via specific RNA splicing.

Antagonists of IRE-1α are useful for treating B-cell autoimmune diseases and cancer. Agonists of IRE-1α are useful for treating Alzheimer's disease and type II diabetes. It would, therefore, be useful to have methods of screening for IRE-1α agonist and antagonist molecules.

BRIEF DESCRIPTION OF THE FIGURES

FIG. 3A, radiant red stain; FIG. 3B, signal from cleaved 15 base FAM substrate. FIG. 3C, radiant red stain.

DETAILED DESCRIPTION OF THE INVENTION

Figure 1:
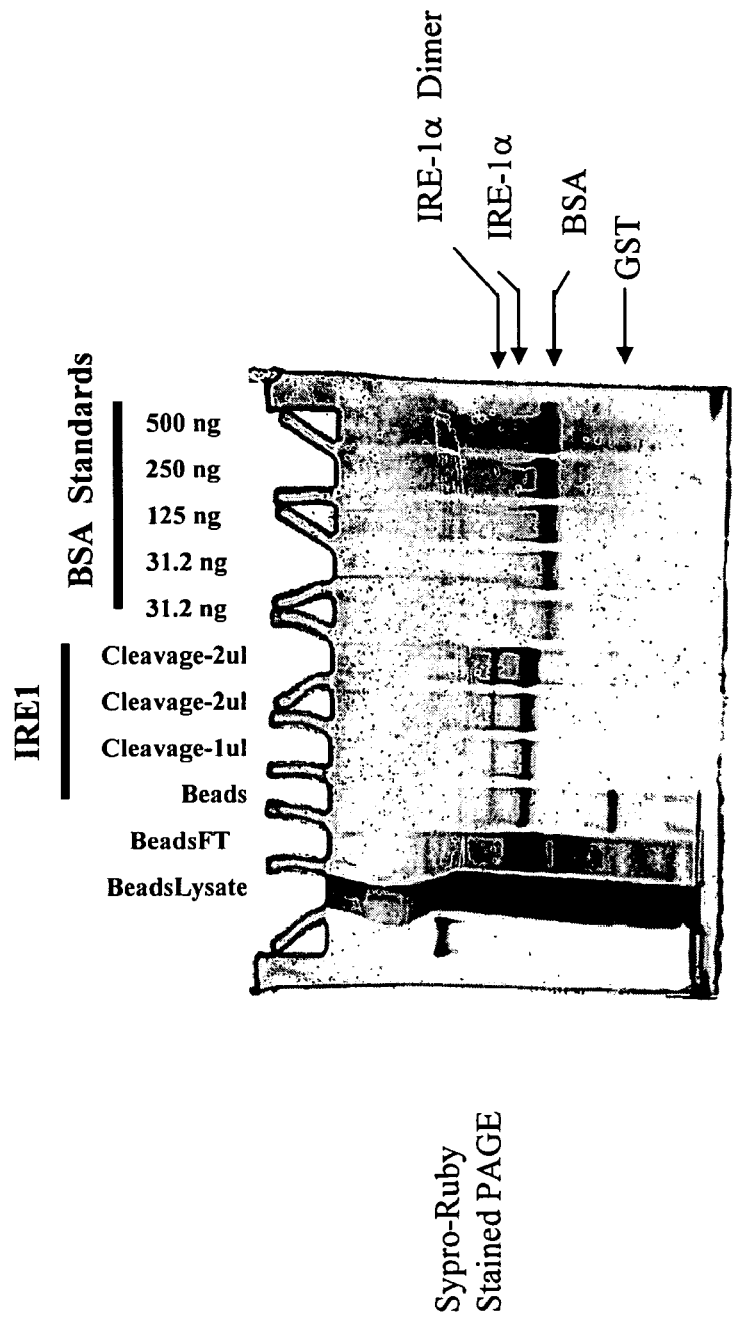
FIG. 1. Spyro ruby-stained polyacrylamide gel showing a purified preparation of IRE-1α monomers and dimers.

The invention provides, inter alia, minimal substrates for IRE-1α which can be used in screening assays of the invention to identify agonists and antagonists of IRE-1α RNase activity, particularly human IRE-1α RNase activity. The invention also provides mutant substrates which IRE-1α does not cleave and which can be used as controls in the screening assays.

IRE-1α substrates according to the invention are oligonucleotide molecules having an RNA loop and a nucleotide stem. The RNA loop contains a cleavage site for IRE-1α, preferably human IRE-1α. In one embodiment, the RNA loop comprises the sequence 5'-CCGCAGC-3' (wild-type). Other useful RNA loops are those in which one or more nucleotides is altered with respect to the wild-type sequence, e.g., 5'-CCGAAGC-3', 5'-GCGAAGC-3', 5'-ACGAAGC-3', 5'-UCGAAGC-3', 5'-CCGAAGC-3', 5'-CGGAAGC-3', 5'-CAGAAGC-3', 5'-CUGAAGC-3', 5'-CCGAAGC-3', 5'-CCAAAGC-3', 5'-CCUAAGC-3', 5'-CCGAAGC-3', 5'-CCGGAGC-3', 5'-CCGUAGC-3', 5'-CCGCAGC-3', 5'-CCGAAGC-3', 5'-CCGAGGC-3', 5'-CCGAUGC-3', 5'-CCGACGC-3, 5'-CCGAAGC-3', 5'-CCGAAAC-3', 5'-CCGAAGC-3', 5'-CCGAAGA-3', and 5'-CCGAAGU-3'. The RNA loop can contain one or more altered nucleotides with respect to the wild-type sequence. If desired, a mutation can be introduced into the RNA loop to form a mutant substrate which IRE-1α cannot cleave. In one embodiment, the RNA loop of the mutant substrate comprises the sequence 5'-CCCCAGC-3'.

Nucleotides in the nucleotide stem can be deoxyribonucleotides, ribonucleotides, and/or nucleotide analogs, such as DNA or phosphorothioates. The nucleotide stem comprises at least 4 and as many as 30 or more nucleotide base pairs. Preferably the nucleotide stem consists of 4, 5, 6, 7, 8, 9, or 10 nucleotide base pairs. The nucleotide stem can have one or more mismatches (bulges) and can have an overhang. The particular nucleotides in the stem are not important as long as at least 4 nucleotide base pairs are formed to stabilize the RNA loop. The basepairs need not be consecutive and may contain one, two, or more mismatches, as long as a stem is formed and one, two, or three basepairs are formed next to the loop.

IRE-1α substrates of the invention can comprise a donor moiety and an acceptor moiety, which permits IRE-1α RNase activity to be detected using resonance energy transfer. The donor moiety is conjugated to one of the 5' or 3' ends of the oligonucleotide molecule, and the acceptor moiety is conjugated to the other of the 5' or 3' ends of the oligonucleotide molecule. In the absence of RNase activity, the donor moiety and the acceptor moiety are in sufficient proximity to each other to exhibit a detectable resonance energy transfer when the donor is excited. The RNase activity of IRE-1α cleaves the substrate, which changes the distance or relative orientation between the donor and acceptor moieties and alters the resonance energy transfer between the moieties. The degree of alteration reflects RNase activity and can be detected qualitatively or quantitatively.

Donor and Acceptor Moieties

As used here, a "donor moiety" is a fluorophore or a luminescent moiety. The absorption spectrum of the "acceptor moiety" overlaps the emission spectrum of the donor moiety. The acceptor moiety does not need to be fluorescent and can be a fluorophore, chromophore, or quencher. In some embodiments both the donor and acceptor moieties are fluorescent proteins. In other embodiments both the donor and acceptor moieties are luminescent moieties. In yet other embodiments, either one of the donor or acceptor moieties can be a fluorescent protein while the other moiety is a luminescent moiety. In other embodiments, the acceptor moiety is a "quencher moiety."

When both the donor and acceptor moieties are fluorophores, resonance energy transfer is detected as "fluorescence resonance energy transfer" (FRET). If a luminescent moiety is involved, resonance energy transfer is detected as "luminescent resonance energy transfer" (LRET) or "bioluminescent resonance energy transfer" (BRET). See Boute et al., Trends Pharmacol. Sci. 23, 351-54, 2002; Ayoub et al., J. Biol. Chem. 277, 21522-28, 2002); US 20050176926;

Lakowicz, Principles of Fluorescence Spectroscopy, Plenum Press, New York pp. 303-339, 1983; Forster, *Annals of Physics* (Leipzig) 2, 55-75, 1948; US 20050191718. Methods of binding donor and acceptor moieties to oligonucleotide molecules are well known in the art. See, e.g., Marras et al., Nucleic Acids Res. 2002 Nov. 1; 30(21): e122; Loeffler et al., J. Clin Microbiol. 2000 February; 38(2): 586-590; Rajendran & Ellington, Nucleic Acids Res. 2003 Oct. 1; 31(19): 5700-5713; and Tyagi & Kramer, Nat. Biotechnol., 14, 303-308, 1996.

Suitable acceptor moieties include, for example, a coumarin, a xanthene, a fluorescein, a fluorescent protein, a circularly permuted fluorescent protein, a rhodol, a rhodamine, a resorufin, a cyanine, a difluoroboradiazaindacene, a phthalocyanine, an indigo, a benzoquinone, an anthraquinone, an azo compound, a nitro compound, an indoaniline, a diphenylmethane, a triphenylmethane, and a zwitterionic azopyridinium compound.

Suitable donor moieties include, but are not limited to, a coumarin, a xanthene, a rhodol, a rhodamine, a resorufin, a cyanine, a bimane, an acridine, an isoindole, a dansyl dye, an aminophthalic hydrazide, an aminophthalimide, an aminonaphthalimide, an aminobenzofuran, an aminoquinoline, a dicyanohydroquinone, a semiconductor fluorescent nanocrystal, a fluorescent protein, a circularly permuted fluorescent protein, and fluorescent lanthanide chelate.

Fluorescent Proteins

In some preferred embodiments either or both of the donor and acceptor moieties is a fluorescent protein. Suitable fluorescent proteins include green fluorescent proteins (GFP), red fluorescent proteins (RFP), yellow fluorescent proteins (YFP), and cyan fluorescent proteins (CFP). Useful fluorescent proteins also include mutants and spectral variants of these proteins which retain the ability to fluoresce.

RFPs include Discosoma RFPs, such Discosoma DsRed (SEQ ID NO:9) or a mutant thereof which includes an Ile125Arg mutation, or a non-oligomerizing tandem DsRed containing, for example, two RFP monomers linked by a peptide linker. For example, a non-oligomerizing tandem RFP can contain two DsRed monomers or two mutant DsRed-I125R monomers linked by a peptide (having, for example, the amino acid sequence shown in SEQ ID NO:10).

Useful GFPs include an *Aequorea* GFP (e.g., SEQ ID NO:11), a *Renilla* GFP, a *Phialidium* GFP, and related fluorescent proteins for example, a cyan fluorescent protein (CFP), a yellow fluorescent protein (YFP), or a spectral variant of the CFP or YFP. CFP (cyan) and YFP (yellow) are color variants of GFP. CFP and YFP contain 6 and 4 mutations, respectively. They are Tyr66Try, Phe66Leu, Ser65Thr, Asn145Ile, Met153Thr, and Val163Ala in CFP and Ser65Gly, Val168Leu, Ser72Ala, and Thr203Tyr. Spectral variants include an enhanced GFP (EGFP; SEQ ID NO:12), an enhanced CFP (ECFP; SEQ ID NO:13), an enhanced YFP (EYFP; SEQ ID NO:14), and an EYFP with V68L and Q69K mutations. Other examples of fluorescent proteins comprising mutations are *Aequorea* GFP with one or more mutations at amino acid residues A206, L221 or F223 of SEQ ID NO:11 (e.g., mutations A206K, L221K, F223R, Q80R); mutations L221K and F223R of ECFP (SEQ ID NO:13), and EYFP-V68L/Q69K of SEQ ID NO:14. See also US 2004/0180378; U.S. Pat. Nos. 6,150,176; 6,124,128; 6,077,707; 6,066,476; 5,998,204; and 5,777,079; Chalfie et al., Science 263:802-805, 1994.

Other useful GFP-related fluorescent proteins include those having one or more folding mutations, and fragments of the proteins that are fluorescent, for example, an *A. victoria* GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in *Aequorea* GFP-related fluorescent proteins improve the ability of the fluorescent proteins to fold at higher temperatures and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO:11, include the substitutions F64L, V68L, S72A, T44A, F99S, Y145F, N146I, M153T, M153A, V163A, 1167T, S175G, S205T, and N212K.

Luminescent Moieties

Luminescent moieties useful in an IRE-1α substrate include lanthanides, which can be in the form of a chelate, including a lanthanide complex containing the chelate (e.g, β-diketone chelates of cerium, praseodymium, neodymium, promethium, samarium, europium, gadolinium, terbium, dysprosium, holmium, erbium, thulium, or ytterbium). Lanthanide chelates are well known in the art. See Soini and Kojola, Clin. Chem. 29, 65, 1983; Hemmila et al., Anal. Biochem. 137, 335 1984; Lovgren et al., In: Collins & Hoh, eds., *Alternative Immunoassays*, Wiley, Chichester, U.K., p. 203, 1985; Hemmila, Scand. J. Clin. Lab. Invest. 48, 389, 1988; Mikola et al., Bioconjugate Chem. 6, 235, 1995; Peruski et al., J. Immunol. Methods 263, 35-41, 2002; U.S. Pat. No. 4,374,120; and U.S. Pat. No. 6,037,185. Suitable β-diketones are, for example, 2-naphthoyltrifluoroacetone (2-NTA), 1-naphthoyltrifluoroacetone (1-NTA), p-methoxybenzoyltrifluoroacetone (MO-BTA), p-fluorobenzoyltrifluoroacetone (F-BTA), benzoyltrifluoroacetone (BTA), furoyltrifluoroacetone (FTA), naphthoylfuroylmethane (NFM), dithenoylmethane (DTM), and dibenzoylmethane (DBM). See also US 20040146895.

Luminescent proteins include, but are not limited to, lux proteins (e.g., luxCDABE from *Vibrio fischerii*), luciferase proteins (e.g., firefly luciferase, *Gaussia luciferase, Pleuromamma* luciferase, and luciferase proteins of other beetles, Dinoflagellates (*Gonyaulax; Pyrocystis*;), Annelids (*Dipocardia*), Molluscs (*Lativa*), and Crustacea (*Vargula; Cypridina*), and green fluorescent proteins of bioluminescent coelenterates (e.g., *Aequorea Victoria, Renilla mullerei, Renilla reniformis*; see Prendergast et al., Biochemistry 17, 3448-53, 1978; Ward et al., Photochem. Photobiol. 27, 389-96, 1978; Ward et al., J. Biol. Chem. 254, 781-88, 1979; Ward et al., Photochem. Photobiol. Rev 4, 1-57, 1979; Ward et al., Biochemistry 21, 4535-40, 1982). Many of these proteins are commercially available. Firefly luciferase is available from Sigma, St. Louis, Mo., and Boehringer Mannheim Biochemicals, Indianapolis, Ind. Recombinantly produced firefly luciferase is available from Promega Corporation, Madison, Wis. Jellyfish aequorin and luciferase from *Renilla* are commercially available from Sealite Sciences, Bogart, Ga.

The DNA sequences of the aequorin and other luciferases employed for preparation of some substrates of the invention can be derived from a variety of sources. For example, cDNA can be prepared from mRNA isolated from the species disclosed above. See Faust, et al., *Biochem.* 18, 1106-19, 1979; De Wet et al., *Proc. Natl. Acad. Sci. USA* 82, 7870-73, 1985.

Luciferase substrates (luciferins) are well known and include coelenterazine (available from Molecular Probes, Eugene, Oreg.) and ENDUREN™. These cell-permeable reagents can be directly administered to cells, as is known in the art. Luciferin compounds can be prepared according to the methods disclosed by Hori et al., *Biochemistry* 14, 2371-76, 1975; Hori et al., *Proc. Natl. Acad. Sci. USA* 74, 4285-87, 1977).

Dark Quenchers

In some embodiments the acceptor moiety is a quencher moiety, preferably a "dark quencher" (or "black hole quencher") as is known in the art. In this case, the change in conformation which occurs with RNase activity eliminates quenching, resulting in an increase in energy emission from the donor moiety. "Dark quenchers" themselves do not emit photons. Use of a "dark quencher" reduces or eliminates background fluorescence or luminescence which would otherwise occur as a result of energy transfer from the donor moiety. Suitable quencher moieties include BLACK HOLE QUENCHER® dyes (e.g., BHQ-0®, BHQ-1®, BHQ-2®, BHQ-3®), which are available from Biosearch Technologies, Inc., and QSY™ dyes available from Invitrogen. Suitable quencher moieties are disclosed, for example, in US 2005/0118619; US 2005/0112673; and US 2004/0146959.

Any suitable fluorophore may be used as the donor moiety provided its spectral properties are favorable for use with the chosen dark quencher. The donor moiety can be, for example, a Cy-dye, Texas Red, a BODIPY™ dye, or an Alexa dye. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, a fluorescein (e.g., fluorescein, tetrachlorofluorescein, hexachlorofluorescein), rhodamine, tetramethylrhodamine, or other like compound. Suitable fluorescent moieties for use with dark quenchers include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS).

Other suitable fluorescent moieties include coumarins, such as 3-phenyl-7-isocyanatocoumarin; acridines, such as 9-isothiocyanatoacridin-e and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethy-loxacarbocyanine (CyA); 1H,5H,1H,15H-Xantheno[2,3,4-ij:5,6,7-i'j']diquinol-izin-18-ium, 9-[2(or 4)-[[[6-[2,5-dioxo-1-pyrrolidinyl)oxy]-6-oxohexyl]amino]sulfonyl]-4(or 2)-sulfophenyl]-2,3,6,7,12,13,16,17-octahydro-inner salt (TR or Texas Red); BODIPY™ dyes; benzoxaazoles; stilbenes; pyrenes; and the like.

Screening Methods

IRE-1α substrates of the invention can be used in a variety of systems to detect, monitor, and quantitate IRE-1α RNase activity. Such assays can be used, for example, to monitor RNase activity or to identify a test compound as an agonist or antagonist of IRE-1α activity. A test compound which increases IRE-1α RNase activity (i.e., an agonist) is a potential therapeutic agent (or lead compound for developing a therapeutic agent) for treating Alzheimer's disease and type II diabetes. A test compound which decreases IRE-1α RNase activity (i.e., an antagonist) is a potential therapeutic agent (or lead compound for developing a therapeutic agent) for treating B-cell autoimmune disease, lupus, and cancer.

Assays can be carried out quantitatively or qualitatively, using either full-length IRE-1α or a portion of IRE-1α comprising the active site for RNase activity, including the cytoplasmic domain and the kinase and RNAse domains. The structure and functional domains of IRE-1α are well understood. See, e.g., Sidrauski & Walter, *Cell* 90, 1-20, 1997; Tirasophon et al., *Genes & Devel.* 14, 2725-2736, 2000; Dong et al., *RNA* 7, 361-73, 2001; Calfon et al., *Nature* 415, 92-202, 2002 Liu et al., *J. Biol. Chem.* 277, 18346-56, 2002; Lee et al., *Mol. Cell. Biol.* 23, 7448-59, 2003; Niwa et al., *Genome Biology* 6, Article R3, 2004; Back et al., *Methods* 35, 395-416, 2005.

In preferred embodiments, changes in resonance energy transfer are used to indicate RNase activity. A change in resonance energy transfer can readily be detected using methods well known in the art. See, e.g., US 2005/0118619; US 2002/0137115; US 2003/0165920; US 2003/0186229; US 2004/0137479; US 2005/0026234; US 2005/0054573; US 2005/0118619; U.S. Pat. No. 6,773,885; U.S. Pat. No. 6,803,201; U.S. Pat. No. 6,818,420; Ayoub et al., 2002; Boute et al., 2002; Domin et al., *Prog. Biomed. Optics and Imaging, Proc. SPIE*, vol 5139, 2003, pp 238-242; Evellin et al., *Methods Mol. biol.* 284, 259-70, 2004; Honda et al., *Proc. Natl. Acad. Sci. USA* 98, 437-42, Feb. 27, 2001; Honda et al., *Methods Mol. Biol.* 3, 27-44, 1005; Mongillo et al., *Cir. Res.* 95, 67-75, Jul. 9, 2004; Mongillo et al., *Methods Mol. Biol.* 307, 1-14, 2005; Nagai et al., *Proc. Natl. Acad. Sci. USA* 101, 10554-59, Jul. 20, 2004; Nikolaev et al., *J. Biol. Chem.* 279, 37215-18, 2004; Polit et al., *Eur. J Biochem.* 270, 1413-23, 2003; Ponsioen et al., *EMBO Rep.* 5, 1176-80, 2004; Santangelo et al., *Nucl. Acids Res.* 32, 1-9, e-published Apr. 14, 2004; and Warrier et al., *Am. J. Physiol. Cell Physiol.* 289, C455-61, August 2005. Properties which can be detected as resonance energy transfer (RET) measurements include a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength.

Other methods can also be used to detect RNase activity. For example, in some embodiments the relative mass of cleaved and uncleaved products is detected, for example, using mass spectroscopy. See, e.g., U.S. Pat. No. 5,506,348. In other embodiments, a detectable label, such as a fluorescent compound, is linked to either the 3' or 5' end of the substrate, and cleavage of the substrate is detected using relative size, such as by capillary electrophoresis. Such methods are well known in the art. See, e.g., Camilleri, ed., Capillary Electrophoresis: Theory and Practice (New Directions in Organic and Biological Chemistry Series), 1997; Heller, Analysis of Nucleic Acids By Capillary Electrophoresis, Chromatographia CE Series Volume 1, 1997; Altria, ed., Capillary Electrophoresis Guidebook: Principles, Operation, and Applications (Methods in Molecular Biology, volume 52), 1996; Guttman et al., *Anal. Chem.* 62, 137-146, 1990; and U.S. Pat. Nos. 5,571,680, 5,110,424, and 5,567,292.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412-421, 1992), or on beads (Lam, *Nature* 354, 82-84, 1991), chips (Fodor, *Nature* 364, 555-556, 1993), bacteria or spores (Ladner, U.S. Pat. No. 5,223,409), plasmids (Cull et al., *Proc. Natl. Acad. Sci. U.S.A.* 89, 1865-1869, 1992), or phage (Scott & Smith, *Science* 249, 386-390, 1990; Devlin, *Science* 249, 404-406, 1990); Cwirla et al., *Proc. Natl. Acad. Sci.* 97, 6378-6382, 1990; Felici, *J. Mol. Biol.* 222, 301-310, 1991; and Ladner, U.S. Pat. No. 5,223,409).

High Through-Put Screening

Screening methods of the invention can be used in high through-put screening formats. Using high throughput screening, many discrete compounds can be tested in parallel so that large numbers of test compounds can be quickly screened. The most widely established techniques utilize 96-well microtiter plates, however 384- or 1536-plates also can be used. As is known in the art, a variety of instruments, materials, pipettors, robotics, plate washers, and plate readers are commercially available.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

Example 1

IRE-1α Protein

A fusion protein comprising glutathione S transferase (GST) and human IRE-1α (GST-IRE-1α) was obtained from a 500 ml baculovirus-infected insect cell culture. The insect cells were lysed by suspending the cells in Buffer A (25 mM Tris-HCl pH7.5, 50 mM KCl, 5 mM MgCl$_2$, 1 mM EDTA, 2.5 mM DTT, 0.1 mM ATP, 10% sterile glycerol, 0.005% NP-40, 1 μg/mL leupeptin, 100 mM NaF, 100 mM NaVO$_4$, 100 mM PMSF; 30 mLs per 500 mL culture), transferring the suspension to a high speed centrifuge tube, and sonicating the suspension on ice. The sonicated preparation was spun at 13000×g for 30 minutes at 4° C.

The supernatant was combined with glutathione Sepharose beads in a tube and gently mixed on a rotator for 1-2 hours at 4° C. After binding, the bead mixture was transferred to an Amersham PD-10 column. The column was washed five times with Buffer A followed by two washes with Buffer B (25 mM Tris-HCl pH7.5, 50 mM KCl, 2.5 mM MgCl$_2$, 1 mM EDTA, 2.5 mM DTT, 10% sterile glycerol, 0.0025% NP-402).

The GST tag was removed using PRESCISSION™ PROTEASE cleavage. Cleavage buffer (825 μL Buffer B, 350 μl sterile glycerol, and 35 μl PRESCISSION™ PROTEASE per mL of beads) was added to the column and incubated for 4 hours at 4° C. with tumbling. The final product was collected by collecting flow-thru from the column. As shown in FIG. 1, this method provides a high yield and a highly pure preparation of IRE-1α protein.

The IRE-1α monomer used in the assays described below (SEQ ID NO:15) comprises amino acids 462-977 of IRE-1α (linker, kinase, and RNAse domains) with GPLGSPEF (amino acids 1-8 of SEQ ID NO: 15) at the end terminus from the linker region of the GST vector.

Example 2

Assay of IRE-1α Activity

An IRE-1α protein preparation obtained as described in Example 1 was tested at various dilutions for RNase activity using four substrates: a 33 base wild-type substrate 5'-GGGUCUGCUGAGUCCGCAGCACUCA-GAAGGCCC-3' (SEQ ID NO:1), a 15 base wild-type substrate 5'-CAGUCCGCAGCACUG-3' (SEQ ID NO:3) labeled with FAM (5') and BHQ-1™ (3'), a 33 base mutant substrate 5'-GGGUCUGCUGAGUCCCCAG-CACUCA-GAAGGCCC-3' (SEQ ID NO:2), and a 15 base mutant substrate 5'-CAGUCCCAGCACUG-3' (SEQ ID NO:4) labeled with FAM (5') and BHQ (3').

Five μl of a reaction mixture comprising 1× reaction buffer (5× reaction buffer is 100 mM Hepes pH 7.5, 250 mM KOAc, 2.5 mM MgCl$_2$), 3 mM DTT, and 0.4% polyethylene glycol water were added to each well of 384 well plates. Twenty-five nanoliters of a 1 mM test compound solution were added to test wells. Three μl of a 128 ng/ml IRE-1α preparation were added to each test well and to positive control wells (final concentration 5.82 ng/well). Negative control wells contained only reaction mixture and test compound.

After spinning the plates at 1200 rpm for 30 seconds, 3 μl of a 63 nM wild-type IRE-1α substrate or 3 μl of a 63 nM mutant IRE-1α substrate diluted to 48 nM were added to each well of a control plate. The plates were again spun at 1200 rpm for 30 seconds. Final concentrations for the assay were: 63 nM wild-type IRE-1α substrate (or 48 nM mutant IRE-α substrate), 5.82 ng IRE-1α protein, and 2.5 μM test compound.

The plates were covered with lids and incubated for one hour at 30° C. The plates were then transferred to an ACQUEST™ microplate reader. Data was analyzed using data analysis software. The percent activity of IRE-1α was calculated using the following equation:

$$\frac{(\text{compound} - \text{mean positive control})}{(\text{mean negative control} - \text{mean positive control})} \times 100\%$$

Figure 3B:
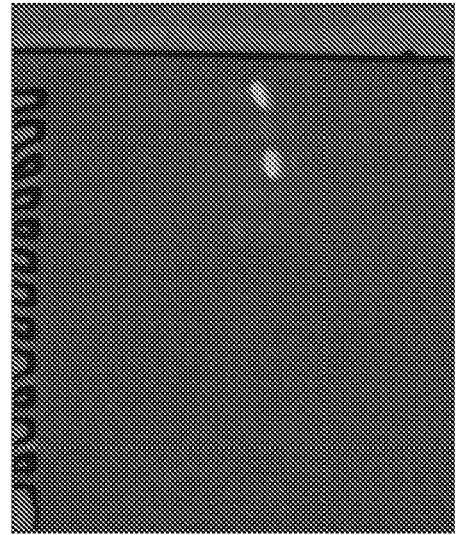
FIGS. 3A-C. Photographs of polyacrylamide gels showing cleavage of an IRE-1α substrate.
Figure 3A:
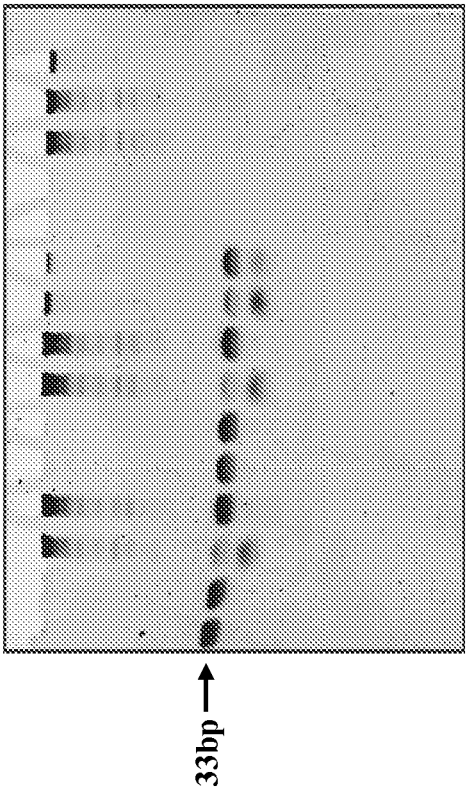

Reaction products were separated on a 20% polyacrylamide urea denaturing gel, which is shown in FIG. 3. From left to right, the lanes are: 1, wild-type 33 base, no IRE-1α; 2, mutant 33 base, no IRE-1α; 3, wild-type 33 pb with IRE-1α (cuts); 4, mutant 33 base with IRE-1α (does not cut); 5, control for adding polyethylene glycol (PEG) to reaction:

wild-type 33 base, no IRE-1α; 6, control for adding polyethylene glycol (PEG) to reaction: mutant 33 base; 7, wild-type 33 pb with IRE-1α (cuts) with PEG; 8, mutant 33 base with IRE-1α (does not cut) with PEG; 9, wild-type 33 pb with IRE-1α diluted 1:3 (cuts) with PEG; 10, wild-type 33 pb with IRE-1α diluted 1:12 (cuts) with PEG; 11, wild-type 15 base FAM-BHQ1 labeled substrate no IRE-1α (no signal); 12, mutant 15 base FAM-BHQ1 labeled substrate no IRE-1α (no signal); 13, wild-type 15 base FAM-BHQ1 labeled substrate with IRE-1α added (signal); 14, mutant 15 base FAM-BHQ1 labeled substrate no IRE-1α (no signal); and 15, wild-type 15 base FAM-BHQ1 labeled substrate with IRE-1α added diluted to 1:3 (signal).

The assays demonstrated that IRE-1α cleaves both wild-type substrates with high specific activity, but does not cleave either of the mutant substrates. The enzyme retains activity at a 1:20 dilution, and the activity appears to be dose dependent.

Figure 2:
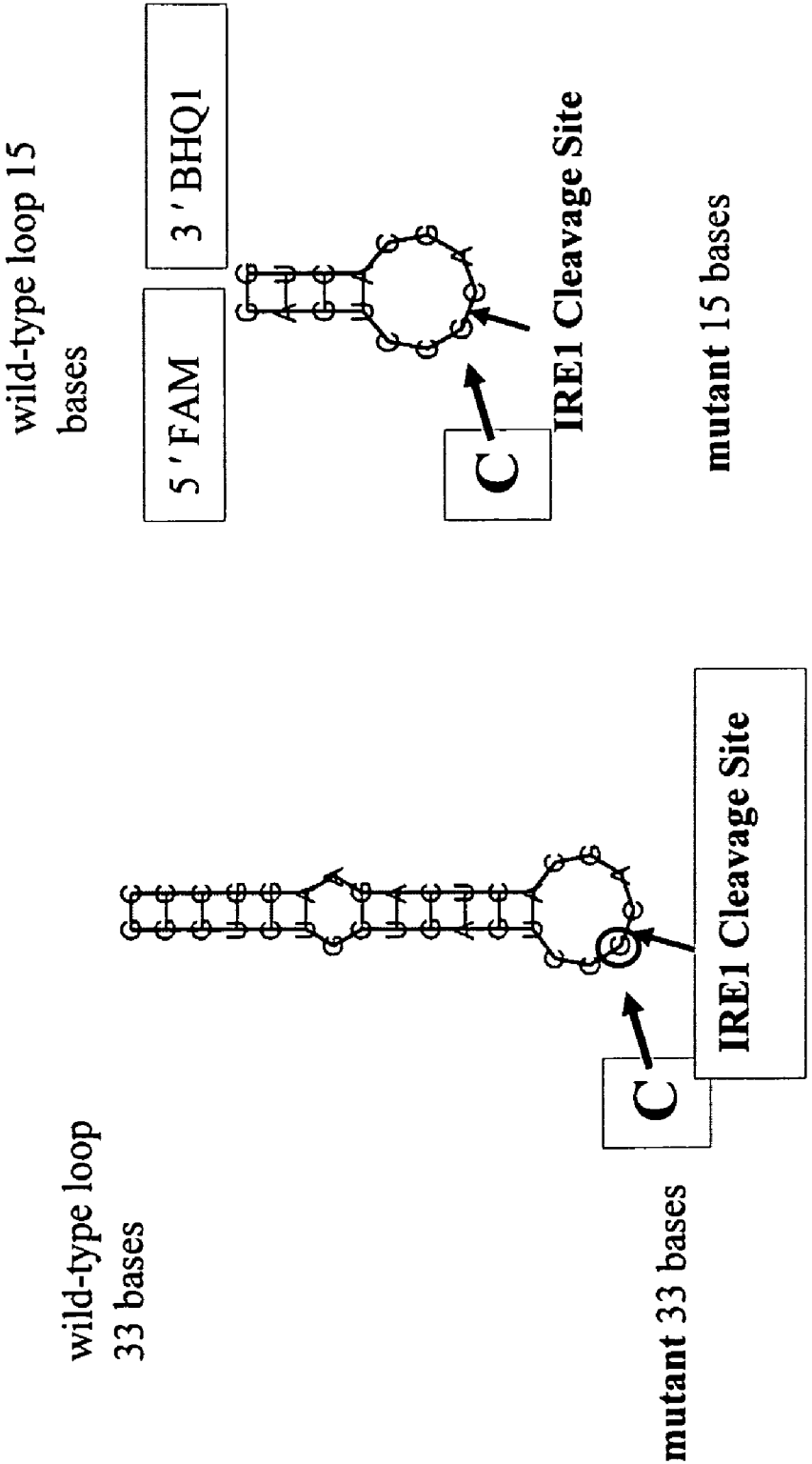
FIG. 2. Drawings of IRE-1α substrates. 33 base wild-type substrate, 5'-GGGUCUGCUGAGUCC-GCAGCACUCA-GAAGGCCC-3' (SEQ ID NO:1); 33 base mutant substrate 5'-GGGUCUGCUGAGUCCCCAGCACUCAGAAG-GCCC-3' (SEQ ID NO:2); 15 base wild-type substrate with 5' FAM and 3' BHQ-1™ moieties (5'-CAGUCCGCAG-CACUG-3', SEQ ID NO:3); 15 base mutant substrate with 5' FAM and 3' BHQ-1™ moieties (5'-CAGUCCCCAG-CACUG-3', SEQ ID NO:4).
Figure 3C:
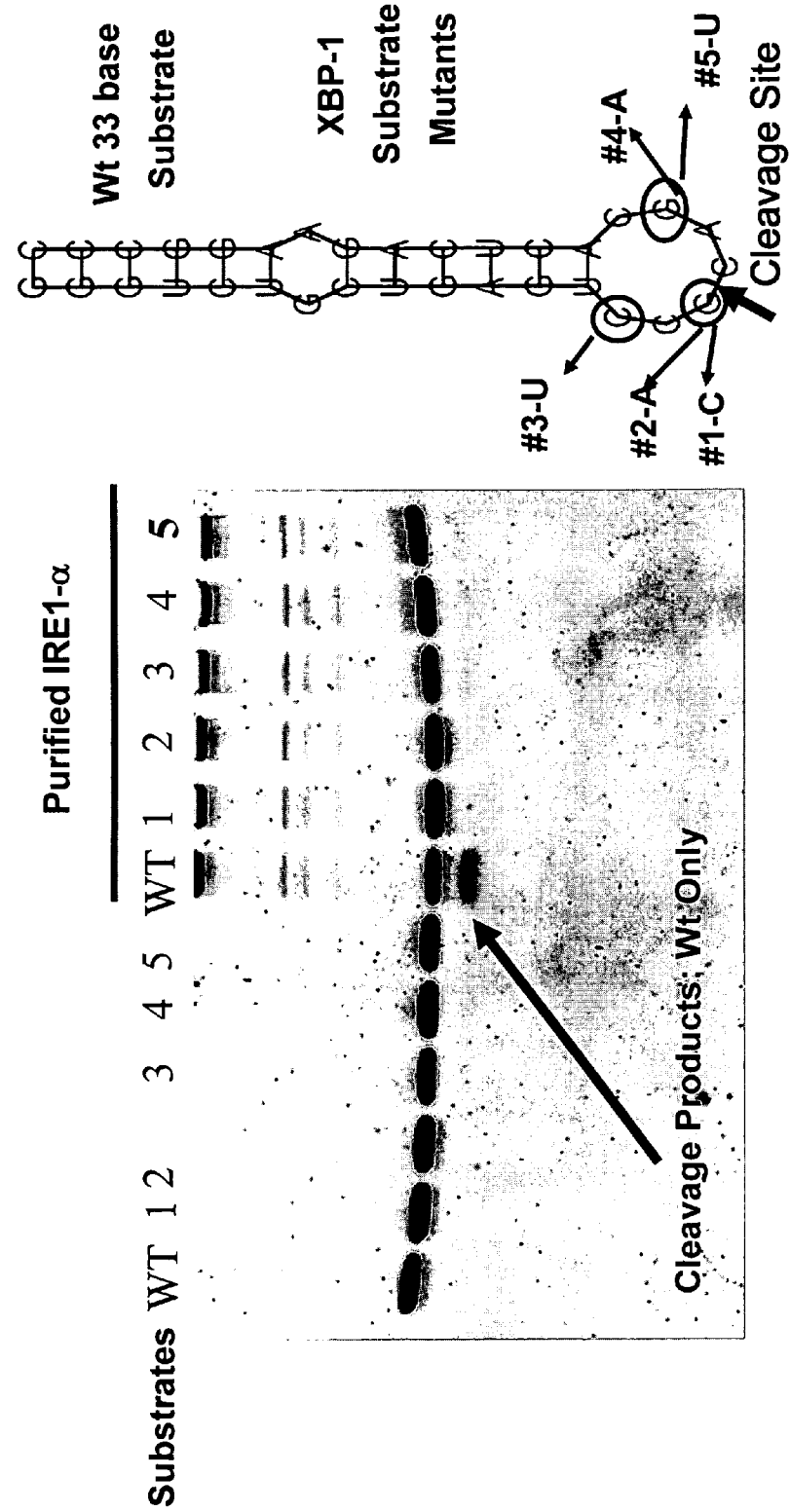

Specific human IRE-1α activity was confirmed using additional 33 base stem-loop substrates with single point mutations in the loop, as shown in FIG. 3C. The structure on the right designates the wild type stem-loop substrate, which also is shown in FIG. 2. Circled residues show wild type residues which were changed to single point mutations (boxed). Mutants are labeled with numbers on the corresponding gel on the left. The experiment was performed in identical fashion as that in FIG. 3A with the exception of using all 5 mutant substrates with or with out the presence of recombinant purified human IRE-1α.

As shown in FIG. 3C, IRE-1α digested the wild type substrate with little if any digestion of the other substrates, indicated by the lack of a lower molecular weight band. From left to right, the lanes are: 1, wild type substrate in reaction buffer, no IRE-1α; 2, mutant substrate #1 in reaction buffer, no IRE-1α; 3, mutant substrate #2 in reaction buffer, no IRE-1α; 4, mutant substrate #3 in reaction buffer, no IRE-1α; 5, mutant substrate #4 in reaction buffer, no IRE-1α; 6, mutant substrate #5 in reaction buffer, no IRE-1α; 7, wild type substrate in reaction buffer, with IRE-1α; 8, mutant substrate #1 in reaction buffer, with IRE-1α; 9, mutant substrate #2 in reaction buffer, with IRE-1α; 10, mutant substrate #3 in reaction buffer, with IRE-1α; 11, mutant substrate #4 in reaction buffer, with IRE-1α; and 12, mutant substrate #5 in reaction buffer, with IRE-1α.

Example 3

Determination of Minimal Substrate Length

Using the assay described above, minimal substrate length was determined using a 15 base substrate (wild-type, SEQ ID NO:3; mutant, SEQ ID NO:4) and an 11 base substrate (wild-type 5'-CUCCCCAGCAG-3', SEQ ID NO:5; mutant 5'-CUCCGCAGCAG-3', SEQ ID NO:6). ATP and ADP are not required for enzyme activity in this assay. GST-IRE-1α is purified in high concentrations of ATP but ultimately this is washed and diluted away to negligible levels.

Example 4

Kinetics of IRE-1α-Mediated Substrate Cleavage

Kinetics of IRE-1α-mediated substrate cleavage were measured in an assay as described above using purified active IRE-1α and the wild-type 15 pb FAM-BHQ-1™-labeled substrate. The plate was incubated at 30° C. and read every 5 minutes.

Figure 4:
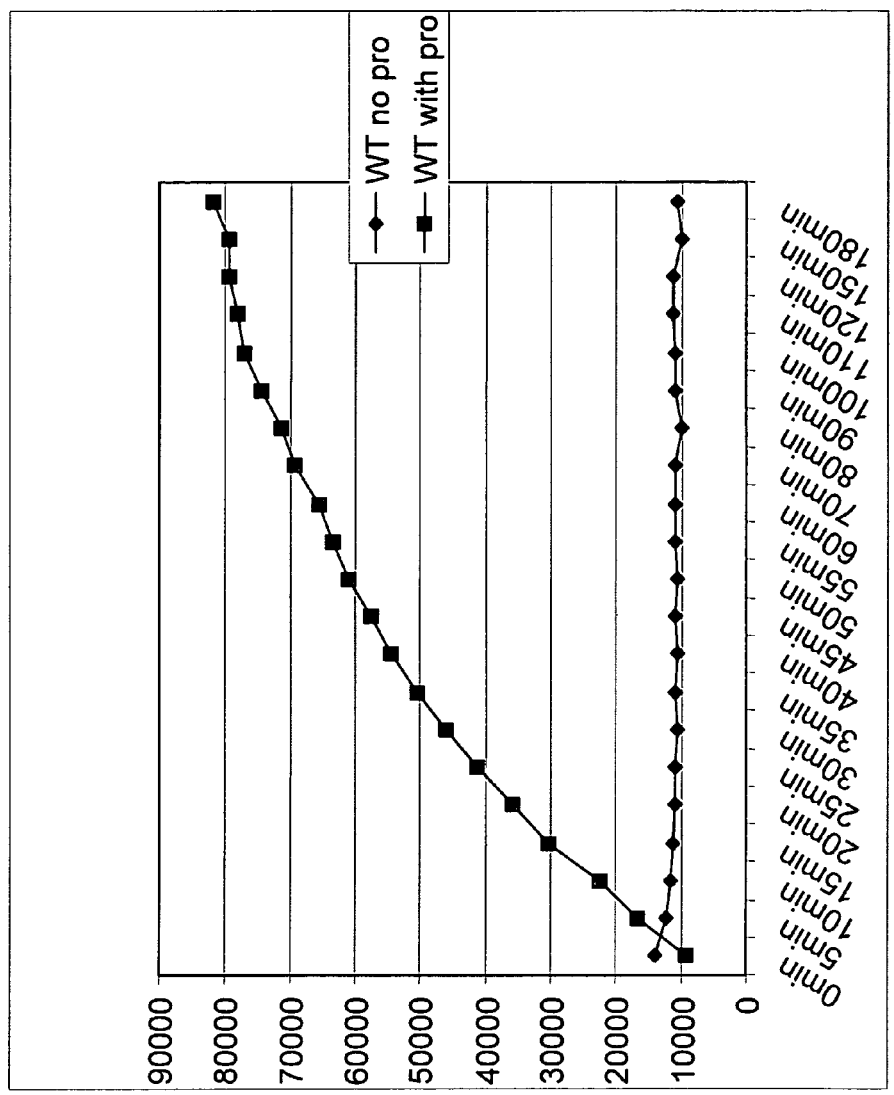
FIG. 4. Graph showing time course of IRE-1α RNase activity at 30° C.

The results are shown in FIG. 4. These data identified useful conditions for a high-throughput assay: 20 nM purified IRE-1α and 63 nM substrate in a 10 µl reaction volume and a 60 minute incubation time. These conditions result in a signal of 60,000 units, which is approximately 75% of the full 80,000 unit signal.

Example 5

Substrate Specificity

This example demonstrates a competition assay using a 15 base wild-type dual-labeled substrate (SEQ ID NO:3) as the readout. Increasing amounts of either unlabeled wild-type (SEQ ID NO:1) or mutant 33 base substrate (SEQ ID NO:2) were incubated in the standard reaction as described in Example 2 for 1 hour at 30° C.

Figure 5:
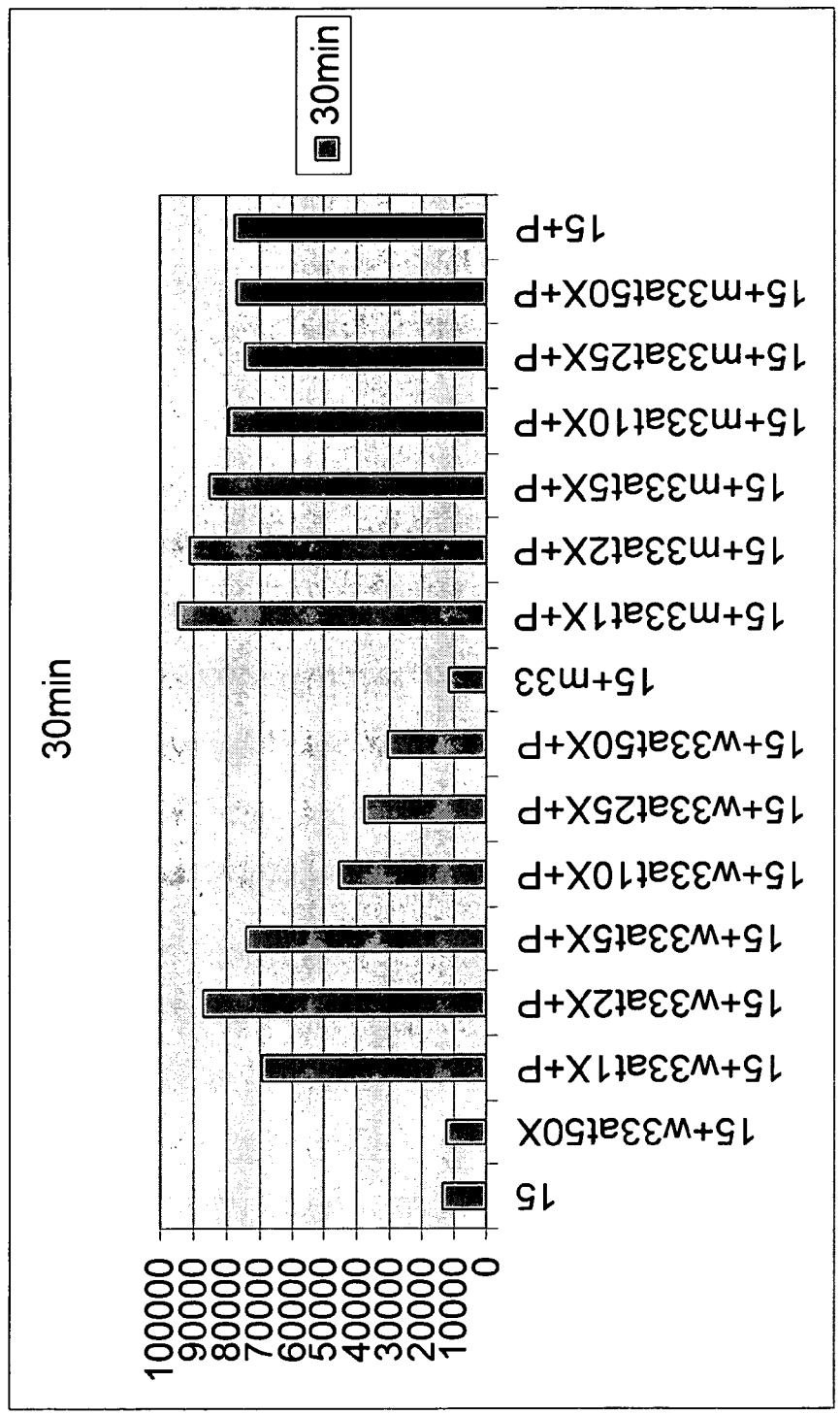
FIG. 5. Bar graph showing results of a competition assay to determine the activity of a 15 base substrate (SEQ ID NO:3) in the presence of a 33 base substrate (SEQ ID NO:1).

The results are shown in FIG. 5. X-axis, fluorescence intensity; columns of Y axis, from left to right: 1, wild-type 15 base FAM BHQ-1™ substrate, no IRE-1α, and no competitor (background signal); 2, wild-type 15 base FAM BHQ-1™ substrate, no IRE-1α (background signal) plus 50 fold molar excess of unlabeled wild-type 33 base substrate (control for possible quenching of fluorophore with excess and possible hybridizing to the longer 33 base substrate); 3, wild-type 15 base FAM BHQ-1™ substrate with IRE-1α and an equivalent amount of wild-type 33 base substrate; 4, same as 3 with 2× wild-type 33 base substrate; 5, same as 3 with 5× wild-type 33 base substrate; 6, same as 3 with 10× wild-type 33 base substrate; 7, same as 3 with 20× wild-type 33 base substrate; 8, same as 3 with 50× wild-type 33 base substrate; 9, wild-type 15 base FAM BHQ-1™ substrate no IRE-1α (background signal) plus 50 fold molar excess of unlabeled mutant 33 base substrate (control for possible quenching of fluorophore with excess and possible hybridizing to the longer 33 base substrate (essentially the same as 2); 10, wild-type 15 base FAM BHQ-1™ substrate with IRE-1α and an equivalent amount of mutant 33 base substrate; 11, same as 3 with 2×33 base mutant substrate; 12, same as 3 with 5×33 base mutant substrate; 13, same as 3 with 10×33 base mutant substrate; 14, same as 3 with 20×33 base mutant substrate; 15, same as 3 with 50×33 base mutant substrate; 16, wild-type 15 base FAM BHQ-1™ substrate with IRE-1α (positive control).

The results show that a ten-fold molar excess of wild-type 33 base substrate begins to compete with the IRE-1α substrate and inhibit fluorescence intensity, with 50-fold excess having greater than 50% inhibitory activity. Similar concentrations of unlabeled 33 base mutant substrate, however, have no inhibitory activity, indicating that IRE-1α does not recognize or bind to the mutant substrate even with a single mutation which preserves its secondary structure. Thus, while the length of the stem has little or no impact on cleavage of the loop, sequence-specific recognition likely is a factor in the catalytic activity of IRE-1α.

Example 6

High-Throughput Screening Assay

Figure 6:
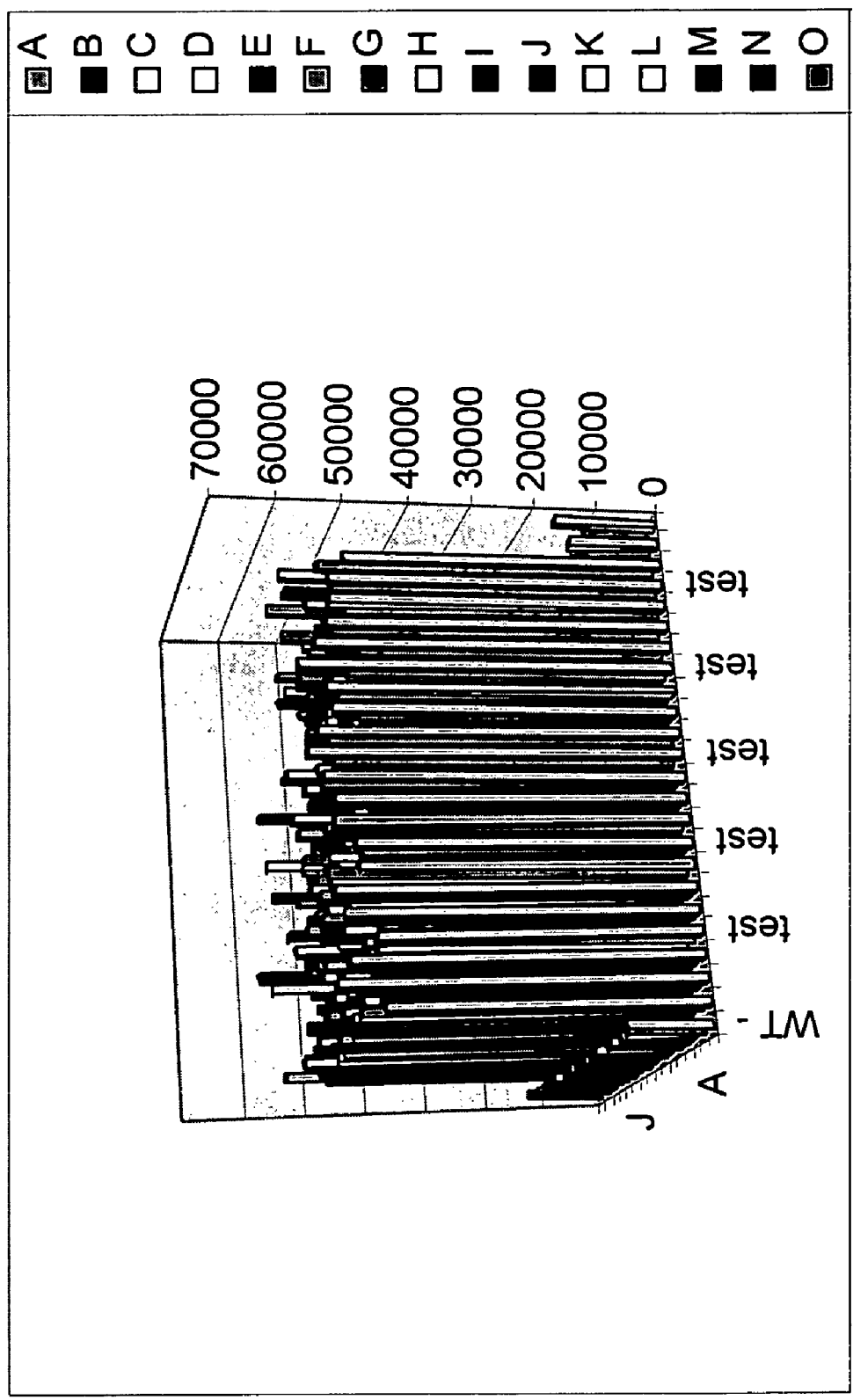
FIG. 6. Graph showing results of a high-throughput assay of IRE-1α RNase activity

A Beckman Biomek FX robot was used to load all components of the reaction into 384-well plates in the following order: buffer with test compound, IRE-1α, and substrate into 384-well plates. The results of the assay and are shown in Table 1 and FIG. 6. Controls with substrate alone and substrate with IRE-1α were used to calibrate signal to noise ratio and variability between wells (first two left hand rows respectively, in FIG. 6). The two far right lanes in FIG. 6 contain the mutant 15 base dual-labeled substrate with and without IRE-1α as a quality control check for RNase contamination.

This example demonstrates that the assay has an acceptable signal increase over background and low variability from well to well and from plate to plate.

TABLE 1

| | wild-type substrate alone | wild-type substrate and IRE-1α | test | mutant substrate alone | mutant substrate and IRE-1α |
|---|---|---|---|---|---|
| average ± std. dev. | 12305 ± 446 | 50076 ± 1418 | 47820 ± 7283 | 10393 ± 312 | 10516 ± 546 |
| CV | 3.6% | 2.8% | 15.2% | 3.0% | 5.2% |
| ratio of positive | | 4.07 | 3.89 | | |

TABLE 1-continued

| | wild-type substrate alone | wild-type substrate and IRE-1α | test | mutant substrate alone | mutant substrate and IRE-1α |
|---|---|---|---|---|---|
| control over background Z' | | 0.85 | | | |

The invention claimed is:

1. A substrate for IRE-1α, comprising:
   (a) an oligonucleotide molecule comprising:
      (i) an RNA loop consisting of a cleavage site for IRE-1α; and
      (ii) a nucleotide stem consisting of 4, 5, 6, 7, 8, 9, or 10 nucleotide base pairs; and
   (b) a donor moiety and an acceptor moiety which exhibit a detectable resonance energy transfer when the donor moiety is excited, wherein the donor moiety is conjugated to one of the 5' or 3' ends of the oligonucleotide molecule and the acceptor moiety is conjugated to the other of the 5' or 3' ends of the oligonucleotide molecule.

2. A substrate for IRE-1α, comprising:
   (a) an oligonucleotide molecule comprising:
      (i) an RNA loop consisting of the nucleotide sequence 5'-CCGCAGC-3'; and
      (ii) a nucleotide stem consisting of 4, 5, 6, 7, 8, 9, or 10 nucleotide base pairs; and
   (b) a donor moiety and an acceptor moiety which exhibit a detectable resonance energy transfer when the donor moiety is excited, wherein the donor moiety is conjugated to one of the 5' or 3' ends of the oligonucleotide molecule and the acceptor moiety is conjugated to the other of the 5' or 3' ends of the oligonucleotide molecule.

3. The substrate of claim 1 wherein the oligonucleotide consists of SEQ ID NO: 3.

4. The substrate of claim 1 wherein the nucleotide stem comprises DNA.

5. The substrate of claim 1 wherein the nucleotide stem comprises RNA.

6. The substrate of claim 1 wherein the nucleotide stem comprises a nucleotide analog.

7. The substrate of claim 1 wherein at least one of the donor and acceptor moieties is a fluorescent protein.

8. The substrate of claim 1 wherein each of the donor and the acceptor moieties is a fluorescent protein.

9. The substrate of claim 1 wherein the acceptor moiety is a luminescent moiety.

10. The substrate of claim 9 wherein the luminescent moiety is selected from the group consisting of a luminescent protein and a lanthanide chelate.

11. The substrate of claim 1 wherein the acceptor moiety is selected from the group consisting of a fluorescent dye, a coumarin, a xanthene, a fluorescein, a fluorescent protein, a circularly permuted fluorescent protein, a rhodol, a rhodamine, a resorufin, a cyanine, a difluoroboradiazaindacene, a phthalocyanine, an indigo, a benzoquinone, an anthraquinone, an azo compound, a nitro compound, an indoaniline, a diphenylmethane, a triphenylmethane, and a zwitterionic azopyridinium compound.

12. The substrate of claim 1 wherein the donor moiety is selected from the group consisting of a fluorescent dye, a non-fluorescent dye, a coumarin, a xanthene, a rhodol, a rhodamines, a resorufin, a cyanine dye, a bimane, an acridine, an isoindole, a dansyl dye, an aminophthalic hydrazide, an aminophthalimide, an aminonaphthalimide, an aminobenzofuran, an aminoquinoline, a dicyanohydroquinone, a semiconductor fluorescent nanocrystal, a fluorescent protein, a circularly permuted fluorescent protein, and a fluorescent lanthanide chelate.

13. The substrate of claim 1 wherein the donor moiety is a fluorescent protein selected from the group consisting of a green fluorescent protein (GFP), a red fluorescent protein (RFP), a yellow fluorescent protein (YFP), a blue fluorescent protein (BFP), and a cyan fluorescent protein (CFP).

14. The substrate of claim 1 wherein the acceptor moiety is a luminescent protein.

15. The substrate of claim 14 wherein the luminescent protein is selected from the group consisting of an aequorin, an obelin, a lux protein, a luciferase protein, a phycobiliprotein, a pholasin, and a green fluorescent protein.

16. A method for detecting RNase activity of an IRE-1α polypeptide, comprising:
   (1) contacting the IRE-1α polypeptide with a substrate, wherein the substrate comprises:
      (a) an oligonucleotide molecule comprising:
         (i) an RNA loop consisting of a cleavage site for IRE-1α;
         (ii) a nucleotide stem consisting of 4, 5, 6, 7, 8, 9, or 10 ribonucleotide base pairs; and
      (b) a donor moiety and an acceptor moiety which exhibit a detectable resonance energy transfer when the donor moiety is excited, wherein the donor moiety is conjugated to one of the 5' or 3' ends of the oligonucleotide molecule and the acceptor moiety is conjugated to the other of the 5' or 3' ends of the oligonucleotide molecule; and
   (2) detecting resonance energy transfer between the donor and acceptor moieties, whereby a change in the resonance energy transfer indicates RNase activity of the IRE-1α polypeptide.

17. The method of claim 16 further comprising detecting the resonance energy transfer in the presence of a test compound.

18. The method of claim 16 wherein the IRE-1α polypeptide and the substrate are in a cell-free system.

19. The method of claim 16 wherein the change in resonance energy is detected by determining a property selected from the group consisting of a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength.

20. The method of claim 16 wherein the IRE-1α polypeptide is a full-length IRE-1α protein.

21. The method of claim 16 wherein the IRE-1α polypeptide comprises a kinase domain.

22. The substrate of claim 1 wherein at least one of the donor and acceptor moieties is a fluorescent dye.

23. The substrate of claim 22 wherein each of the donor and acceptor moieties is a fluorescent dye.

24. The substrate of claim 1 wherein the donor moiety is a xanthene.

25. The substrate of claim 24 wherein the xanthene is 6-carboxyfluorescein (FAM).

26. The substrate of claim 1 wherein the donor moiety is a cyanine.

27. The substrate of claim 26 wherein the cyanine is indodicarbocyanine 5 (Cy5).

28. The substrate of claim 1 wherein the acceptor moiety is a dark quencher.

29. The substrate of claim 28 wherein the dark quencher is a QSY™ dye.

30. The substrate of claim 28 wherein the dark quencher is a BLACK HOLE QUENCHER® (BHQ®).

31. The method of claim 16 wherein at least one of the donor and acceptor moieties is a fluorescent dye.

32. The method of claim 16 wherein each of the donor and acceptor moieties is a fluorescent dye.

33. The method of claim 16 wherein the acceptor moiety is a dark quencher.

34. The method of claim 16 wherein the acceptor moiety is selected from the group consisting of a QSY™ dye and a BLACK HOLE QUENCHER® (BHQ®).

35. The method of claim 16 wherein the acceptor moiety is selected from the group consisting of BHQ-1®, BHQ-2, and BHQ-3®.

36. The method of claim 16 wherein the donor moiety is selected from the group consisting of 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX), sulforhodamine 101 (Texas Red), indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyloxacarbocyanine (CyA), 9-isothiocyanatoacridine, acridine orange, and N-(p-(2-benzoxazolyl)phenyl)maleimide.

37. The method of claim 36 wherein the donor moiety is indodicarbocyanine 5 (Cy5).

38. The method of claim 36 wherein the donor moiety is 6-carboxyfluorescein (FAM).

39. The method of claim 16 wherein the donor is a fluorescent dye and the acceptor is a dark quencher.

40. The substrate of claim 1 wherein the RNA loop consists of a nucleotide sequence selected from the group consisting of: 5'-CCGAAGC-3', 5'-GCGAAGC-3', 5'-ACGAAGC-3', 5'-UCGAAGC-3', 5'-CCGAAGC-3', 5'-CGGAAGC-3', 5'-CAGAAGC-3', 5'-CUGAAGC-3', 5'-CCGAAGC-3', 5'-CCAAAGC-3', 5'-CCUAAGC-3', 5'-CCGAAGC-3', 5'-CCGGAGC-3', 5'-CCGUAGC-3', 5'-CCGCAGC-3', 5'-CCGAAGC-3', 5'-CCGAGGC-3', 5'-CCGAUGC-3', 5'-CCGACGC-3', 5'-CCGAAGC-3', 5'-CCGAAAC-3', 5'-CCGAAGC-3', 5'-CCGAAGA-3', and 5'-CCGAAGU-3'.

41. The substrate of claim 2 wherein the donor moiety is a cyanine.

42. The substrate of claim 41 wherein the cyanine is indodicarbocyanine 5 (Cy5).

43. The substrate of claim 2 wherein the acceptor moiety is a dark quencher.

44. The substrate of claim 43 wherein the dark quencher is a QSY™ dye.

45. The substrate of claim 43 wherein the dark quencher is a BLACK HOLE QUENCHER® (BHQ®).

46. The substrate of claim 1 wherein the 1 nucleotide stem consists of 4 nucleotide base pairs.

47. The substrate of claim 1 wherein the 1 nucleotide stem consists of 5 nucleotide base pairs.

48. The substrate of claim 1 wherein the 1 nucleotide stem consists of 6 nucleotide base pairs.

49. The substrate of claim 1 wherein the 1 nucleotide stem consists of 7 nucleotide base pairs.

50. The substrate of claim 1 wherein the 1 nucleotide stem consists of 8 nucleotide base pairs.

51. The substrate of claim 1 wherein the 1 nucleotide stem consists of 9 nucleotide base pairs.

52. The substrate of claim 1 wherein the 1 nucleotide stem consists of 10 nucleotide base pairs.

\* \* \* \* \*

UNITED STATES PATENT AND TRADEMARK OFFICE
CERTIFICATE OF CORRECTION

| | | |
|---|---|---|
| PATENT NO. | : 8,017,331 B2 | Page 1 of 1 |
| APPLICATION NO. | : 11/266603 | |
| DATED | : September 13, 2011 | |
| INVENTOR(S) | : Patterson et al. | |

It is certified that error appears in the above-identified patent and that said Letters Patent is hereby corrected as shown below:

Column 8, Line 65:
  Delete "33 pb" and insert --33 base--

Column 9, Line 3:
  Delete "33 pb" and insert --33 base--

Column 9, Line 4:
  Delete "33 pb" and insert --33 base--

Column 9, Line 5:
  Delete "33 pb" and insert --33 base--

Column 9, Line 62:
  Delete "15 pb" and insert --15 base--

Signed and Sealed this
Eleventh Day of October, 2011

David J. Kappos
*Director of the United States Patent and Trademark Office*